United States Patent [19]

Lantz

[11] Patent Number: 4,845,300
[45] Date of Patent: Jul. 4, 1989

[54] SYNTHESIS OF 2-(PERFLUOROALKYL) ETHANETHIOLS

[75] Inventor: André Lantz, Vernaison, France
[73] Assignee: Societe Atochem, Puteaux, France
[21] Appl. No.: 141,847
[22] Filed: Jan. 11, 1988

[30] Foreign Application Priority Data

Jan. 13, 1987 [FR] France .................. 87 00290

[51] Int. Cl.$^4$ .......................... C07C 149/16
[52] U.S. Cl. ........................................... 568/65
[58] Field of Search ............................ 568/65, 69

[56] References Cited

U.S. PATENT DOCUMENTS

| 3,088,849 | 5/1963 | Friedlander | 558/5 |
| 3,172,910 | 3/1965 | Brace | 568/65 |
| 3,544,663 | 12/1970 | Haupstschein et al. | 558/250 |

FOREIGN PATENT DOCUMENTS

2018461 4/1970 Fed. Rep. of Germany .
2083422 12/1971 France .
2113219 6/1972 France .

OTHER PUBLICATIONS

E. Reid, Organic Chemistry of Bivalent Sulfur, vol. 1, pp. 32-35, Chemical Publishing Co., N.Y. (1958).
Organic Syntheses, Collective, vol. 3, New York, John Wiley & Sons, Inc., London, pp. 362-365.

*Primary Examiner*—Mary E. Ceperley
*Attorney, Agent, or Firm*—Stevens, Davis, Miller & Mosher

[57] ABSTRACT

The subject of the invention is a process for the preparation of 2-(perfluoroalkyl)ethanethiols $R_fCH_2CH_2SH$, $R_f$ denoting a straight-chain or branched perfluoroalkyl radical containing from 2 to 20 carbon atoms. The processes comprises reacting a 2-(perfluoroalkyl)ethyl iodide with thiourea and then decomposing the isothiouronium salt formed with an alkaline base, and is characterized in that it is carried out in a non-alcoholic inert solvent.

2 Claims, No Drawings

SYNTHESIS OF 2-(PERFLUOROALKYL) ETHANETHIOLS

FIELD OF THE INVENTION

The present invention relates to the production of 2-(perfluoroalkyl)ethanethiols which may be represented by the formula:

$$R_f CH_2 CH_2 SH$$

in which $R_f$ denotes a straight-chain or branched perfluoroalkyl radical which may contain from 2 to 20 carbon atoms.

BACKGROUND OF THE INVENTION

These compounds are synthesis intermediates used for the production of fluorinated surfactants and of products for the hydrophobic and oleophobic treatment of substrates such as textiles and leathers.

These thiols have already been described and are generally obtained by reacting a 2-(perfluoroalkyl)ethyl iodide $R_f C_2 H_4 I$ with thiourea, followed by the alkaline hydrolysis of the thiouronium salt thus obtained:

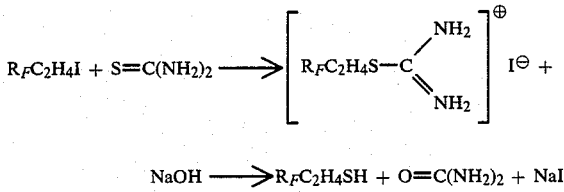

$$\text{NaOH} \longrightarrow R_f C_2 H_4 SH + O=C(NH_2)_2 + NaI$$

This preparation process is the use of a method which is conventional for converting alkyl iodides and bromides into the corresponding thiol. For non-fluorinated thiols, this method has widely been described, mainly starting with alkyl bromides, which are more readily available than the iodides. The condensation of the halide with thiourea is generally carried out in an alcoholic or aqueous-alcoholic medium to achieve a homogeneous reaction medium. See E. Reid, *Organic Chemistry of Bivalent Sulfur*, Vol. I., page 32–35, Chemical Publishing Co., New York, 1958, and *Organic Syntheses*, coll. Vol. 3, page 363, hereby incorporated by reference.

Many patents describe the preparation, according to the same process, of 2-(perfluoroalkyl)ethanethiols $R_f C_2 H_4 SH$. There may be mentioned, for example, U.S. Pat. Nos. 3,088,849; 3,544,663; and 3,172,910; as well as French Pat. Nos. 2,083,422; and 2,113,219. All these documents present examples for the preparation of these 2-(perfluoroalkyl)ethanethiols by decomposing the isothiouronium salts obtained by reacting 2-(perfluoroalkyl)ethyl iodides $R_f C_2 H_4 I$ with thiourea. In all these examples, this reaction is always carried out in an alcoholic (methanol, ethanol, isopropanol or butanol) medium, probably with a view to being able to solubilize the two reagents as well as the isothiouronium salt.

Although 2-(perfluoroalkyl)ethanethiols, especially those containing a relatively long $R_f$ chain (for example $C_6 F_{13}$) only have a weak odor of mercaptans, this method of preparation in an alcoholic medium always leads unfortunately to the formation of foul-smelling by-products. These make the process virtually unuseable on an industrial scale in a conventional plant. Essentially, foul-smelling by-products are formed during the second reaction stage, i.e., during the alkaline decomposition of the isothiouronium salt.

SUMMARY OF THE INVENTION

It has now been found that virtually no foul-smelling by-products are formed when the synthesis of 2-(perfluoroalkyl)ethanethiols by reacting a 2-(perfluoroalkyl)ethyl iodide with thiourea followed by the alkaline hydrolysis of the isothiouronium salt is carried out in a non-alcoholic solvent.

DETAILED DESCRIPTION OF THE INVENTION

Any non-alcoholic solvent may be suitable provided that it is inert. Thus, the solvent does not react with the different reagents and reaction products as well as is capable of dissolving at least partially the reagents and the reaction products.

As non-limiting examples of suitable solvents, there may be mentioned dioxane, acetonitrile, ethylene glycol or diethylene glycol dialkyl ($C_1$–$C_4$) ethers as well as mixtures of these solvents with one another or with water.

A particularly advantageous solvent is 1,2-dimethoxyethane which may be used alone or in admixture with water. It is possible for the proportion of water in the mixture to range up to 40% by weight. This proportion is preferably between 10.5 and 20%. 1,2-dimethoxyethane is perfectly compatible with the different reaction products. The reaction may be carried out in this solvent or in its mixture with water even if all the reagents and/or the isothiouronium salt are not completely soluble therein. Moreover, the volatility of the solvent (b.p. = 84° C.; b.p. of the azeotrope containing 10.5% of water = 76° C.) enables it to be recovered very easily and to be reused in a subsequent operation. When the reaction is carried out in such a solvent, no gaseous or liquid effluents are formed which are as foul-smelling as those formed in the reaction carried out in an alcoholic medium.

The quantity of solvent to be used may vary within wide limits, provided that it is sufficient to permit the fluidification and therefore the stirring of the reaction medium. It is generally between 0.1 and 2 liters (preferably between 0.15 and 0.4 liter) per mole of $R_f C_2 H_4 I$.

Regarding the rest of the procedure, the process according to the invention may be performed under usual operating conditions.

The quantity of thiourea is advantageously chosen so as to be able to convert completely the $R_f C_2 H_4 I$ which is an expensive reagent. The molar ratio thiourea: $R_f C_2 H_4 I$ may range from 1 to 1.5 and is preferably between approximately 1.05 and 1.2.

The condensation of $R_f C_2 H_4 I$ with thiourea may be carried out at a temperature between 40° C. and the reflux temperature and preferably between 80° and 100° C.

The alkaline reagent to be used for the decomposition of the isothiouronium salt may be, for example, sodium hydroxide or potassium hydroxide, liquid ammonia or a water-soluble primary, secondary, or tertiary amine such as ethylamine, n-propylamine, diethylamine, trimethylamine, or mono-, di- or triethanolamine. This reagent may be used in a quantity ranging from 1 to 1.5 mole, preferably from 1 to 1.2 mole, per mole of $R_f C_2 H_4 I$. This decomposition may be carried out at a temperature ranging from 40° to 110° C., preferably between 60° and 80° C., and is advantageously carried out in an aqueous medium.

Because the thiols can be readily oxidized into the disulphides $(R_fC_2H_4S)_2$, it is advantageous to carry out the whole process and in particular the final stage (decomposition of the isothiouronium salt) in an inert gas atmosphere, preferably a nitrogen atmosphere.

After separating the reaction mixture by phase-separation, a washing of the crude product with water generally makes it possible to obtain thiols having a purity about 95% which may be used as such for the subsequent manufacture of finished products. This washing is preferably carried out with hot water, or with water which is slightly acid and at a temperature such that the thiol is liquid. If desired, a distillation enables thiols having a purity much greater than 99% to be obtained.

EXAMPLES

The following examples in which the percentages referred to are percentages by weight, illustrate the invention without limiting it.

Example 1

The following substances are introduced into a reactor equipped with an efficient stirrer and fitted with a distillation column from above:

580 g (1 mole) of a mixture of $R_fC_2H_4I$ containing approximately 32.8% of $C_6F_{13}C_2H_4I$
28.8% of $C_8F_{17}C_2H_4I$
23.4% of $C_{10}F_{21}C_2H_4I$
9.6% of $C_{12}F_{25}C_2H_4I$
3.9% of $C_{14}F_{29}C_2H_4I$
1.5% of $C_{16}F_{33}C_2H_4I$ 83.6 g (1.1 mole) of thiourea,
200 cm³ of 1,2-dimethoxyethane, and
20 g of water.

The mixture is then heated to slight reflux (85° to 90° C.) under a nitrogen atmosphere. It becomes homogeneous very quickly and then gradually becomes thicker so as to form a gel after a few hours. The reaction is complete after 8 hours of heating. $R_fC_2H_4I$ content, as determined by chromatographic analysis, is less than 1%.

After cooling to 70° C. and still under a nitrogen atmosphere, 85 g (1 mole) of 20% ammonia solution are introduced gradually into the reactor (over approximately one hour), while maintaining the temperature at 70° C. at the same time. The pasty reaction medium undergoes change to give a mixture of two liquid phases.

By separating the lower organic phase and after washing with 2×250 cm³ of water at 95° C., 460 g of a mixture of thiols $R_fC_2H_4SH$ which becomes solid below 50° C. and which contains, in addition of $R_fC_2H_4SH$, approximately 2% of disulphides $(R_fC_2H_4S)_2$ as determined by chromatographic analysis, are obtained.

Example 2

474 g (1 mole) of $C_6F_{13}C_2H_4I$, 84 g (1.1 mole) of thiourea and 200 cm³ of p-dioxane are introduced into a 1-liter reactor equipped with an efficient stirrer and fitted with a distillation column from above. The mixture is heated to reflux (105° C.) under a nitrogen atmosphere for 4 hours. A chromatographic monitoring makes it possible to check that the amount of unconverted $C_6F_{13}C_2H_4I$ remaining is less than 0.5%.

After cooling to 80° C., a mixture of 44 g of sodium hydroxide and 200 g of water is then added over one hour. The reaction mixture is then acidified with 25 g of 37% hydrochloric acid, which enables the thiol to be settled.

The heavy phase is separated off. It is washed with 2×300 g of water at 90° C. 360 g of the thiol $C_6F_{13}C_2H_4SH$ are thus obtained as a crude product-containing 4% of disulphide $(C_6F_{13}C_2H_4S)_2$.

During this preparation, no significant amounts of foul-smelling products are formed.

I claim:

1. A process for the preparation of 2-(perfluoroalkyl)ethanethiols of formula:

$$R_fCH_2CH_2SH$$

in which $R_f$ denotes a straight-chain or branched perfluoroalkyl radical containing from 2 to 20 carbon atoms, comprising reacting a 2-(perfluoroalkyl)ethyl iodide with thiourea, followed by alkaline decomposition of the isothiouronium salt formed, characterized in that the reaction is carried out in a non-alcoholic inert solvent, in which the solvent is dioxane, acetonitrile, an ethylene glycol or diethylene glycol dialkyl ether or a mixture of these solvents with one another or with water.

2. The process according to claim 1, in which the solvent is 1,2-dimethoxyethane.

* * * * *